Figure 1:
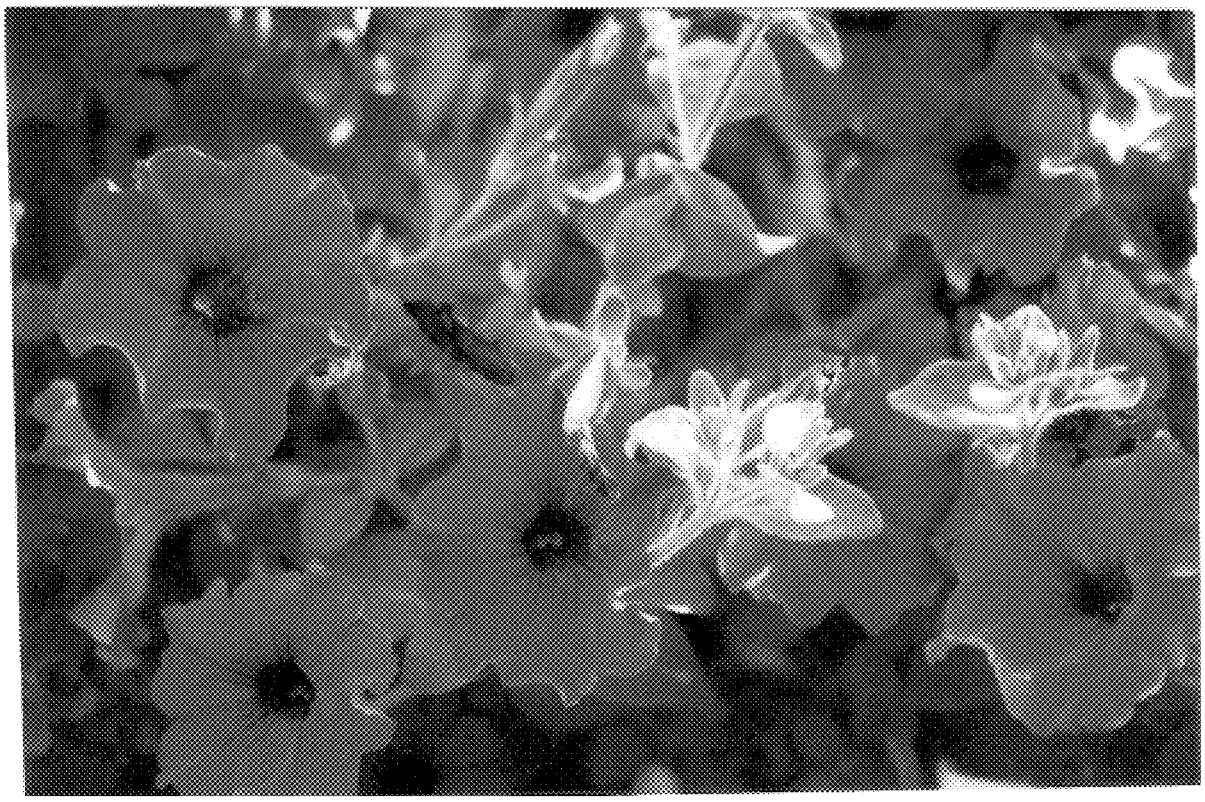

US00PP11573P

United States Patent [19]

Westhoff

[11] Patent Number: Plant 11,573

[45] Date of Patent: Oct. 17, 2000

[54] PETUNIA PLANT NAMED 'WESPUR'

[75] Inventor: Heinrich Westhoff, Südlohn-Oeding, Germany

[73] Assignee: Josef + Heinrich Westhoff Gartenbau-Spezialkulturen, Sudlohn-Oeding, Germany

[21] Appl. No.: 09/213,448

[22] Filed: Dec. 17, 1998

[51] Int. Cl.[7] ..... A01H 5/00

[52] U.S. Cl. ..... Plt./356

[58] Field of Search ..... Plt./356

*Primary Examiner*—Howard J. Locker
*Assistant Examiner*—Michelle Kizilkaya
*Attorney, Agent, or Firm*—C. A. Whealy

[57] ABSTRACT

A distinct cultivar of Petunia plant named 'Wespur', characterized by its compact plant habit; relatively small leaves; numerous purple flowers; cascading and freely branching growth habit; early flowering; and good weather tolerance, particlarly tolerant to rain, wind and low temperatures.

2 Drawing Sheets

BACKGROUND OF THE INVENTION

The present invention relates to a new and distinct cultivar of Petunia plant, botanically known as *Petunia×hybrida*, and hereinafter referred to by the cultivar name 'Wespur'.

The new Petunia is a product of a planned breeding program conducted by the Inventor in Südlohn-Oeding, Germany. The new Petunia originated from a cross made by the Inventor in 1996 in Südlohn-Oeding, Germany, of a seedling selection of *Petunia×hybrida* identified as Sylvana 95/304 as the female, or seed, parent with the nonpatented *Petunia×hybrida* cultivar Sylvana Purple as the male, or pollen parent.

Asexual reproduction of the new cultivar by terminal cuttings taken at Südlohn-Oeding, Germany, has shown that the unique features of this new Petunia are stable and reproduced true to type in successive generations.

SUMMARY OF THE INVENTION

Plants of the cultivar Wespur have not been observed under all possible environmental conditions. The phenotype may vary somewhat with variations in environment such as temperature, light intensity, daylength, and fertility level without, however, any variance in genotype.

The following traits have been repeatedly observed and are determined to be the unique characteristics of 'Wespur'. These characteristics in combination distinguish 'Wespur' as a new and distinct cultivar:

1. Compact plant habit.
2. Relatively small leaves.
3. Numerous purple flowers.
4. Cascading and freely branching growth habit.
5. Relatively early flowering.
6. Good weather tolerance, particularly tolerant to rain, wind and low temperatures.

Plants of the cultivar Wespur are similar in flower color to plants of the nonpatented 'Surfinia Purple'. However in side-by-side comparisons conducted in Südlohn-Oeding, Germany, plants of the cultivar Wespur differ from plants of the cultivar Surfinia Purple in the following characteristics:

1. Plants of the new Petunia are more compact than of plants of the cultivar Surfinia Purple.
2. Leaves of plants of the new Petunia are smaller than leaves of plants of the cultivar Surfinia Purple.

3. Plants of the new Petunia have more but smaller flowers than plants of the cultivar Surfinia Purple.
4. Plants of the new Petunia flower earlier than plants of the cultivar Surfinia Purple.
5. Plants of the new Petunia exhibit better weather tolerance, particularly to rain, than plants of the cultivar Surfinia Purple.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

FIG. 1 comprises a side perspective view of typical flowers of the new Petunia.

Figure 2:
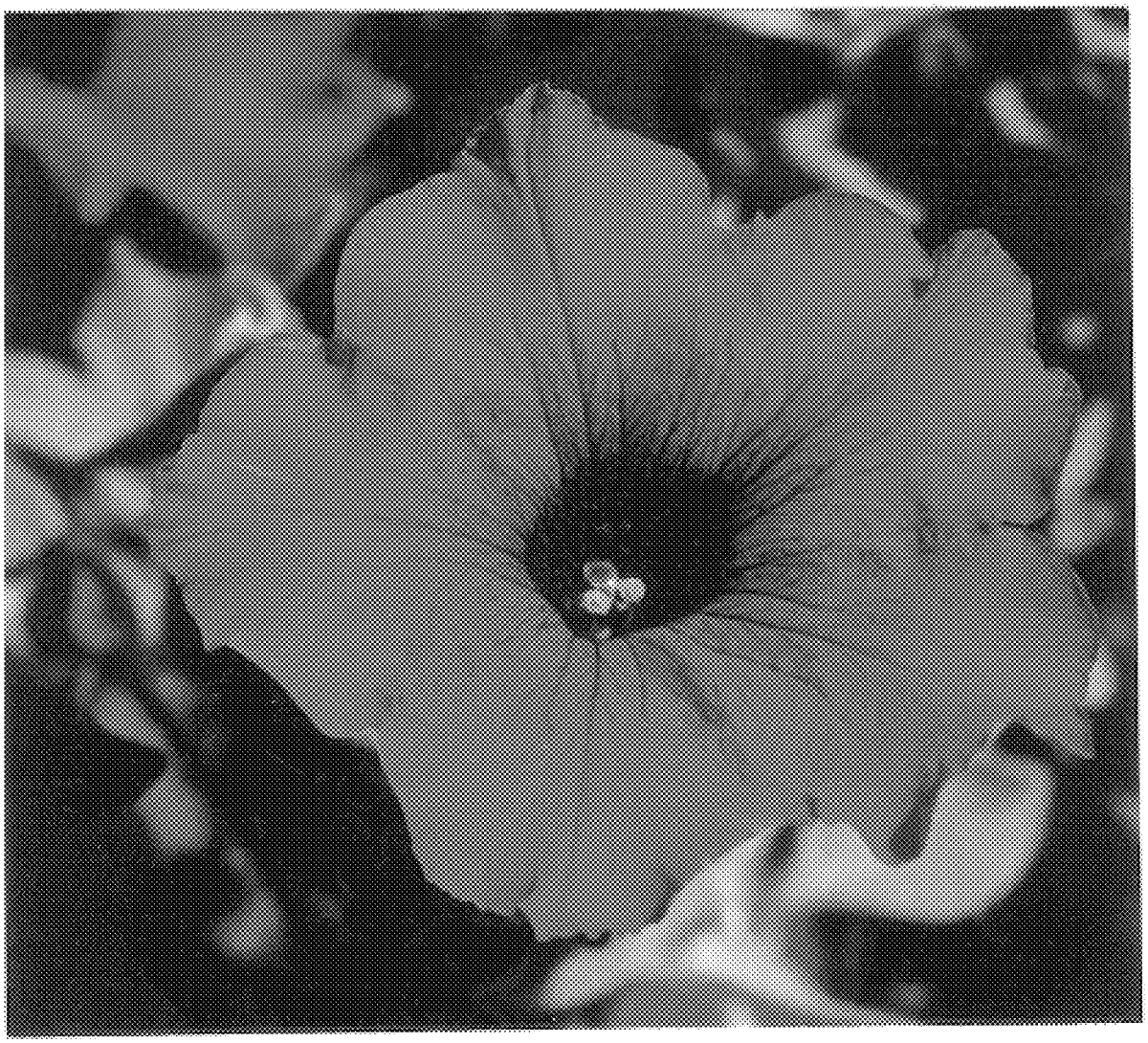

FIG. 2 comprises a close-up view of a typical flower of the new Petunia. Flower and foliage colors in the photographs may appear different than the actual colors due to light reflectance.

DETAILED BOTANICAL DESCRIPTION

In the following description, color references are made to The Royal Horticultural Society Colour Chart except where general terms of ordinary dictionary significance are used. Twelve-week old plants grown in 12.5-cm containers used for the description were grown under greenhouse conditions which closely approximate commercial production conditions in Südlohn-Oeding, Germany, with average day and night temperatures of 23° C. and 26° C., respectively with an average light level ranging from 3,000 to 50,000 lux.

Botanical classification: *Petunia×hybrida* cultivar Wespur.

Parentage:

*Female parent.*—*Petunia×hybrida* seedling selection identified as Sylvana 95/304, not patented.

*Male parent.*—*Petunia×hybrida* cultivar Sylvana Purple, not patented.

Propagation:

*Type Cutting.*—Terminal vegetative cuttings.

*Time to initiate and develop roots.*—About 14 days at 20° C. soil temperature.

*Rooting habit.*—Numerous, fine, fibrous, and well-branched.

Plant description:

*Form.*—Indeterminate, decumbent, cascading, viscid, glandular pubescent. Appropriate for hanging baskets.

*Branching habit.*—Freely basally branching, lateral branches typically form at every node.

*Plant height* (*from soil level to top of plant plane*).—About 6 cm.

*Area of spread.*—About 76 cm, cascading, decumbent.

*Vigor.*—Moderate.

*Lateral branches.*—Quantity: Typically 10. Length: About 44 cm. Diameter: About 2.6 mm. Internode length: About 3.2 cm. Texture: Moderately pubescent. Color: 144A.

*Foliage description.*—Leaves simple, generally symmetrical and long persisting. Leaf arrangement alternate before flowering, opposite after flowering. Leaves smewhat fleshy, glandular, Foliage tolerant to wind and rain damage. Quantity per lateral branch: Typically about 25. Length: About 4.2 cm. Width: About 2.8 cm. Aspect: Typically horizontal. Shape: Obovate. Apex: Slightly acute to rounded. Base: Attenuate. Margin: Entire. Texture: Slightly pubescent on both surfaces. Clor: Young foliage, upper surface: 138A. Young foliage, lower surface: 138B. Mature foliage, upper surface: 137A. Mature foliage, lower surface: 137D. Venation, both surfaces: 138B. Petiole: Length: About 9 mm. Diameter: About 2 mm. Color: 138B.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall.

*Quantity.*—Very freely flowering with numerous flowers per plant.

*Flower buds.*—Length: About 3.53 cm. Diameter: About 5.3 mm. Shape: Oblong. Color: Apex: 79B. Mid-section: 195A. Base: 79B.

*Corolla.*—Diameter: About 5.7 cm. Flower tube length: About 2.66 cm. Flower tube diameter at distal end: About 1.15 cm. Flower tube diameter at proximal end: About 3 mm. Petal length from throat: About 2.75 cm. Petal width: About 3.1 cm. Petal quantity: Five, fused. Petal apex: Rounded and slightly dentate. Texture: Smooth and satiny. Color: Petal, upper surface, when opening: 83A. Petal, lower surface, when opening: 83C. Petal, upper surface, opened flower: 78A. Petal, upper surface, vein: 202A. Petal, lower surface, opened flower: 78C. Petal, lower surface, vein: 79B. Flower throat (inside): 79B. Flower throat, vein: 202A. Flower tube (outside): 79B. Flower tube, vein: 79B. Petal color, fading to: 83A.

*Sepals.*—Quantity: Five. Length: About 1.8 cm. Width: About 4.2 mm. Shape: Linear. Apex: Obtuse. Margin: Entire. Aspect: Upright. Texture: Pubescent. Color: Upper surface: 146A. Lower surface: 146B.

*Peduncle.*—Strength: Wiry, flexible. Angle: About 31° to stem. Length: About 2.56 cm. Width: Narrow, about 1.5 mm. Texture: Pubescent. Color: 143C with slight anthocyanin color, 177A, near the flower.

*Reproductive organs.*—Stamens: Stamen number: Five. Anther shape: Four-parted, roughly oval. Anther size: About 2.7 mm. Anther color: 79D. Pollen amount: Moderate to abundant. Pollen color: 90D. Pistils: Pistil length: About 2.2 cm. Stigma shape: Inverted triangle. Stigma color: 79A. Style length: About 1.9 cm. Style color: 143C. Ovary color: 143B.

Weather tolerance: Good tolerance to rain and wind has been observed. The new Petunia can withstand low temperatures to about −3° C.

Disease resistance: Resistance to diseases common to Petunia has not been observed.

Seed production: Seed production has not been observed.

It is claimed:

1. A new and distinct cultivar of Petunia plant named 'Wespur', as illustrated and described.

* * * * *